US00PP08479P

United States Patent [19]

Henny

[11] Patent Number: Plant 8,479

[45] Date of Patent: Nov. 30, 1993

[54] MANDEVILLA "WHITE DELITE"

[75] Inventor: Richard J. Henny, Tavares, Fla.

[73] Assignee: Gem Ornamentals, Inc., Tavares, Fla.

[21] Appl. No.: 765,949

[22] Filed: Sep. 26, 1991

[51] Int. Cl.[5] ..... A01H 5/00

[52] U.S. Cl. ..... Plt./54.1

[58] Field of Search ..... Plt./54.1

*Primary Examiner*—James R. Feyrer
*Assistant Examiner*—Erich E. Veitenheimer
*Attorney, Agent, or Firm*—Merchant, Gould, Smith, Edell, Welter & Schmidt

[57] ABSTRACT

A new and distinct variety of Mandevilla characterized by medium-sized white flowers, shiny, dark evergreen leaves and branching growth habit.

1 Drawing Sheet

BACKGROUND OF THE INVENTION

This invention relates to a new and distinct variety of Mandevilla that originated from self-pollinating the hybrid Mandevilla X 'Alice du Pont'. Mandevilla X 'Alice du Pont' is a hybrid from a cross of [*M. splendens* X (unknown species)] X *M. splendens* according to Bailey (see reference noted below).

This new Mandevilla is the result of deliberate self-pollination performed by the inventor in a greenhouse at Gem Ornamentals in Tavares, Fla. in 1989. This new variety was selected for further evaluation because it had a white flower color. The new variety has been reproduced by asexual propagation using cuttings. Each of the progeny exhibits identical characteristics to the original mother plant establishing this hybrid as reproducible and true to type.

This new variety is neither like any Mandevilla commercially available nor any of those described in the following publications:

Bailey, L. H. and E. Z. Bailey; *Hortus Third,* Macmillian, New York, 1976.

Graf, A. B.; *Color Cyclopedia of Exotic Plants and Trees,* Rohers Co. East Rutherford, N.J., 1978.

Unlike currently available Mandevilla, the present invention has the following unusual characteristics:

1. White flowers — that open pale pink, fade to white within 1-2 days after anthesis and remain on the plant an additonal 3-4 days;

2. Growth habit that exhibits moderate axillary branching once flowering has been initiated; and 3. Linear to elliptically shaped, leathery, shiny dark green and evergreen leaves.

BRIEF DESCRIPTION OF THE DRAWINGS

The accompanying photographs which illustrate the present invention are as follows.

DETAILED DESCRIPTION OF THE INVENTION

Figure 1:
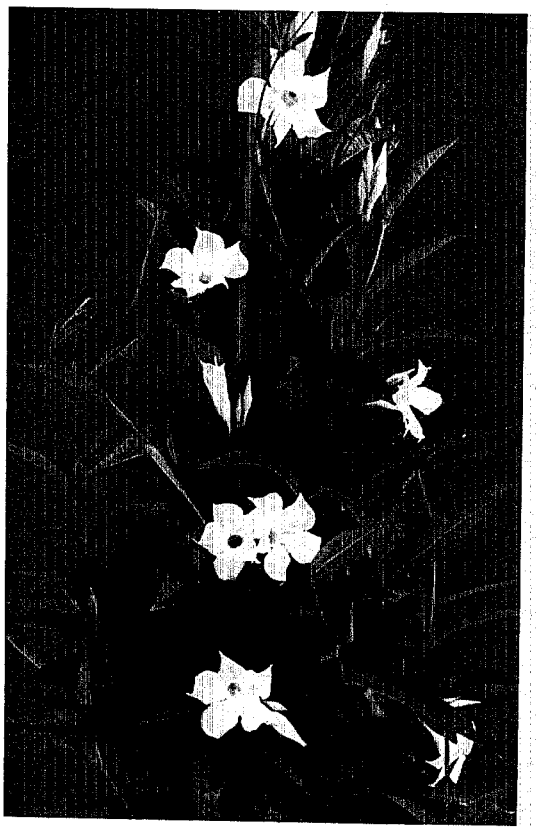
FIG. 1 is a frontal view of a 4-month-old plant of the invention showing its white flowers, shiny leaves and vining growth habits.

The following is a detailed description of the new Mandevilla plant based on observations of the specimen plants grown in Tavares, Fla. as shown in the accompanying photographs. The color determinations and comparisons are all based on The Royal Horticultural Society Colour Chart.

Overall size and growth habit:

*Size.*—The ultimate size of the new variety is unknown as no plant has reached full maturity. The new hybrid has grown between 1 to 1.5 meters in two months under greenhouse conditions in the summer in Tavares, Fla.

*Growth habit.*—The growth habit is a woody twining vine with evergreen, linear to elliptic leaves and large funnel form to trumpet-shaped white flowers borne in axillary clusters on new growth. Plants exhibit moderate axillary branching along the vine once flowering begins. Stems remain green and are minutely hairy.

Foliage:

*Type.*—Evergreen, herbaceous.

*Shape.*—Linear to elliptic.

*Length.*—12 cm to 16 cm.

*Width.*—3 cm to 5.5 cm.

*Petiole length.*—0.5 cm to 1.2 cm.

*Margins.*—Entire, slightly undulate.

*Apex.*—Acuminate.

*Base.*—Cordate.

*Texture.*—Leathery, minutely hairy.

*Leaf arrangement.*—Opposite.

*Venation.*—Pinnate, slightly sunken midribs and veins.

*Color.*—Upper Leaf surface — R.H.S. Colour Chart Fan 3, Group, No. 137A. Upper midrib — R.H.S. Colour Chart Fan 3, Green Group, No. 138B. Lower leaf surface — R.H.S. Colour Chart Fan 3, Yellow-green Group No. 146A. Lower midrib — R.H.S. Colour Chart Fan 3, Yellow-green Group, No. 145C.

Flowers:

*Arrangement.*—Lateral, axillary racemes producing flowers throughout the flowering season (May through October). Individual racemes 5-7 flowered. Inflorescense longer than subtending leaves.

*Structure.*—Bisexual, stamens borne on corolla, anthers connivent, adhering to stigma. Corolla width.—8 to 10 cm. Tube and throat length.—3.5 to 4.5 cm. Corolla lobes rounded with accuminate tips.

*Habit.*—Diurnal, remaining on plant 5-6 days.

*Color.*—Corolla opens pale-pink, R.H.S. Colour Chart Fan 2, Red-Purple Group, No. 62D, but fades to white R.H.S. Colour Chart Fan 4, White Group, No. 155D within 2 days. Accuminate corolla tips also open pale pink R.H.S. Colour Chart Fan 2 Red-Purple Group, No. 62C, but also fades to white, R.H.S. Colour Chart Fan 4, White Group, No. 155D, within two days. Throat color opens striated light pink, R.H.S. Colour Chart Fan 2, Red-Purple Group, No. 62C, and fades to striated pale pink, R.H.S. Colour Chart Fan 2, Red-purple Group No. 62D, after one day. Yellowish coloration, R.H.S. Colour Chart Fan 1, Green-Yellow Group 1C, is also visible at the base of the throat around the stamens on a mature flower.

i Fragrance.—None.

Tubers: The tubers taken from a 1-year-old plant were irregular in shape varying from cylindrical to globose with constrictions occurring at irregular intervals. The diameter was between 0.5 and 2.0 cm. Their color was R.H.S. Colour Chart Fan 4, Grey-Brown Group, No. 199A.

Fruit and seed: No fruit or seed have been observed on this variety.

Cold hardiness: This new variety has withstood temperatures of 34° F. but is not frost tolerant.

In contrast, the original parent plant and its differences from the present invention are readily apparent from the following description of the parent plant:

Mandevilla X 'Alice du Pont':

*Leaf shape.*—Elliptic-oblong to ovate-oblong.

*Leaf length.*—10 cm to 13 cm, not as long as the new variety.

*Leaf width.*—4 cm to 6.5 cm, wider than the new variety.

*Petiole length.*—0.4 cm to 0.7 cm, shorter than the new variety.

*Stem and lower leaf surfaces.*—Beginning 7.5 cm to 12.5 cm from the growing tip, the lower leaf surfaces, midribs and/or stem show a pinkish-red pigmentation. No such pinkish-red pigmentation occurs on the lower leaf surface, midribs and/or stems of the new variety. Stems of the new variety are green as previously described.

*Corolla width.*—9.5 cm to 11.5 cm, wider than the new variety.

*Tube and throat length.*—5 cm to 5.7 cm, longer than the new variety.

*Flower color.*—Corolla opens pink, R.H.S. Colour Chart Fan 2, Red-Purple group No. 63C, but darkens to deep pink, R.H.S. Colour Chart Fan 2, Red-Purple group No. 63A. The new variety opens pale pink and lightens to white as previously described. Throat color opens striated dark pink R.H.S. Colour Chart Fan 2, Red-Purple group No. 64C and darkens to No. 63A. New variety's throat opens R.H.S. Colour Chart Fan 2, Red-Purple No. 62C, and lightens to 62D. White, R.H.S. Colour Chart Fan 4, White Group No. 155B, is also visible at the base of the throat around the stamens on a mature flower. The new variety's throat is yellow-green as previously described.

*Fragrance.*—Faint.

Having thus described my invention, I claim:

1. A new and distinct variety of Mandevilla plant substantially as shown and described, characterized by:

flowers that open pale pink and become white within two days and last an additional 3–4 days on the plant;

moderate axillary branching once the plant reaches flowering size; and shiny, dark green linear to elliptically-shaped leaves on the plant.

* * * * *